United States Patent [19]
Graf et al.

[11] Patent Number: 5,565,599
[45] Date of Patent: Oct. 15, 1996

[54] STABILISED DITHIOPHOSPHORIC ACID POLYSULPHIDES

[75] Inventors: Hans-Joachim Graf, Mannheim; Lothar Steger, Munich; Klaus Knörr, Böhl-Iggelheim; Hartmut Schulz, Heidelberg; Volker Schäfer, Altrip; Thomas Scholl, Bergisch Gladbach; Rüdiger Schubart, Bergisch Gladbach; Manfred Schweiger, Bürstadt, all of Germany

[73] Assignee: Rhein Chemie Rheinau GmbH, Mannheim, Germany

[21] Appl. No.: 518,684

[22] Filed: Aug. 24, 1995

[30] Foreign Application Priority Data

Sep. 6, 1994 [DE] Germany .................. 44 31 727.1

[51] Int. Cl.$^6$ .................. C07F 9/02; C09K 3/00
[52] U.S. Cl. .................. 558/71; 558/151; 252/182.17
[58] Field of Search ............ 558/151, 71; 252/182.17

[56] References Cited

U.S. PATENT DOCUMENTS

| | | | |
|---|---|---|---|
| 4,496,495 | 1/1985 | Caspari et al. | 558/71 |
| 5,208,362 | 5/1993 | Glass et al. | 558/146 |

FOREIGN PATENT DOCUMENTS

| | | |
|---|---|---|
| 0383102 | 8/1990 | European Pat. Off. . |
| 2249090 | 4/1973 | Germany . |

OTHER PUBLICATIONS

T. Biswas et al., *Kautsch. Gummi, Kunstst.* ©(1993), 46(2), 125–8.
Plast., Rubber Compos. Process. Appl. 20:179–184 (1993).
Chem. Abstr., 061078; 79:555 (1973).

*Primary Examiner*—Johann Richter
*Assistant Examiner*—Laura L. Stockton
*Attorney, Agent, or Firm*—Connolly & Hutz

[57] ABSTRACT

Disclosed herein are stabilized dithiophosphoric acid polysulphides of the formula (I)

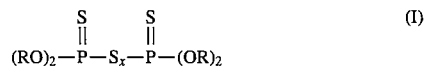

in which
R is a $C_1$–$C_{20}$ alkyl, cycloalkyl, aryl or aralkyl residue and x is an integer from 2 to 15,
containing as stabilizer 1 to 20 wt.% of a carboxylic acid of the general formula R'COOH, in which R' is a $C_1$–$C_{20}$ alkyl residue, a cycloalkyl residue, an aryl residue or an aralkyl residue, and 1 to 20 wt.% of calcium oxide or zinc oxide.

1 Claim, No Drawings

STABILISED DITHIOPHOSPHORIC ACID POLYSULPHIDES

Dithiopnosphoric acid polysulphides are known, as is their use as vulcanising agents or vulcanisation accelerators for rubber vulcanisation (c.f. DDR patent 228 722, DE-OS 22 49 090 and EP-A 383 102). Since it is difficult to comply with guide values for atmospheric nitrosamines during rubber vulcanisation, there is particular interest in rubber auxiliaries which have good vulcanisation activity but which form no hazardous decomposition products, in particular no nitrosamines. Dithiophosphoric acid polysulphides occupy an important position in this respect.

Dithiophosphoric acid polysulphides may be produced from the sodium salts of the corresponding dithiophosphoric acids and disulphur dichloride ($S_2Cl_2$). They are greenish yellow oils having an unpleasant mercaptan-like odour and readily decompose eliminating hydrogen sulphide, especially in the presence of water.

The dithiophosphoric acid polysulphides are of the formula $$(RO)_2-\overset{\underset{\|}{S}}{P}-S_x-\overset{\underset{\|}{S}}{P}-(OR)_2 \quad (I)$$

in which
R is a $C_1$–$C_{20}$ alkyl residue, a cycloalkyl residue, an aryl residue or an aralkyl residue and
x means an integer from 2 to 15.
The residues R are preferably a $C_4$–$C_8$ alkyl residue x is preferably 4 to 6 and very particularly preferably 4.

The present invention provides dithiophosphoric acid polysulphides of the formula (I) which have been stabilised against thermal and hydrolyric decomposition by the addition of 1 to 20 wt.% of a monocarboxylic acid of the formula R'COOH, with R' being $C_1$–$C_{20}$ alkyl, cycloalkyl, aryl or aralkyl, and 1 to 20 wt.% of calcium oxide or zinc oxide, in each case relative to the mixture.

The stabilised products are light yellow, virtually odourless oils which undergo no decomposition even in an aqueous medium and when exposed to heat.

The stabilising carboxylic acid and oxides may be added to the dithiophosphoric acid polysulphides in any desired manner. They are preferably added immediately after production and, preferably, both carboxylic acids and metal oxides are used. It is here again preferred first to add the carboxylic acid and then the metal oxide.

Preferred stabilised dithiophosphoric acid polysulphides are, for example, dibutyldithiophosphoric acid polysulphide, di-2-ethylhexyldithiophosphoric acid polysulphides, preferred carboxylic acids are, for example, 2-ethylhexanoic acid, n-hexanoic acid, coconut palm kernel oil fatty acid and the preferred metal oxide is zinc oxide. The stabilising quantities of the carboxylic acids are 1 to 20%, preferably 1 to 5%, relative to the mixture and the quantities of the metal oxide are likewise 1 to 20, preferably 1 to 5 wt.%, relative to the mixture.

The stabilised dithiophosphoric acid polysulphides may be used for vulcanising rubbers in the same manner as unstabilised products without any impairment of activity. The advantages of the stabilised products reside in their insensitivity to heat and water, the reduction of unpleasant odours and, above all, in their more reliable meterability.

EXAMPLE

Stabilisation of dibutyldithiophosphoric acid polysulphide 200 g of dibutyldithiophosphoric acid are initially introduced into a flask with 60 g of water and slowly stirred together with 124 g of sodium hydroxide solution (25%). After 1 hour's stirring at room temperature, 52 g of disulphur dichloride are slowly added dropwise. Stirring of the mixture is continued for approximately 2 hours and the aqueous phase is separated from the organic phase in a separating funnel. 8 g of 2-ethylhexanoic acid and then 8 g of zinc oxide are added to the organic phase. The resultant mixture is maintained at 70° C. for two hours under a vacuum and then filtered through diatomaceous earth.

Yield: 220 g of yellow, low-odour oil.

We claim:
1. A stabilized composition containing:
dithiophosphoric acid polysulphides of the formula (I)

$$(RO)_2-\overset{\underset{\|}{S}}{P}-S_x-\overset{\underset{\|}{S}}{P}-(OR)_2$$

in which
R is a $C_1$–$C_{20}$ alkyl, cycloalkyl, aryl or aralkyl residue and
x is an integer from 2 to 15,
and containing as stabilizer 1 to 20 wt% of a carboxylic acid of the general formula R'COOH, in which R' is a $C_1$–$C_{20}$ alkyl residue, a cycloalkyl residue, an aryl residue or an aralkyl residue, and
1 to 20 wt% of calcium oxide or zinc oxide.

* * * * *